(12) United States Patent
Leach

(10) Patent No.: US 7,705,005 B2
(45) Date of Patent: Apr. 27, 2010

(54) BICYCLIC HETEROAROMATIC COMPOUNDS

(75) Inventor: Colin Andrew Leach, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 152 days.

(21) Appl. No.: 11/626,882

(22) Filed: Jan. 25, 2007

(65) Prior Publication Data

US 2008/0090853 A1    Apr. 17, 2008

(51) Int. Cl.
*A61K 31/517*    (2006.01)
(52) U.S. Cl. .................. 514/266.22; 544/287; 546/199
(58) Field of Classification Search ............ 514/266.22; 544/287; 546/199
See application file for complete search history.

(56) References Cited

U.S. PATENT DOCUMENTS

| | | | |
|---|---|---|---|
| 6,649,619 | B1 | 11/2003 | Hickey et al. |
| 7,153,861 | B2 | 12/2006 | Hickey et al. |
| 7,169,924 | B2 | 1/2007 | Elliott et al. |
| 7,232,902 | B2 | 6/2007 | Mulholland et al. |
| 7,235,566 | B2 | 6/2007 | Hickey et al. |
| 2002/0103213 | A1 | 8/2002 | Hickey et al. |
| 2004/0063753 | A1 | 4/2004 | Hickey et al. |
| 2005/0043335 | A1 | 2/2005 | Elliott et al. |
| 2005/0153964 | A1 | 7/2005 | Leach |
| 2005/0245552 | A1 | 11/2005 | Leach et al. |
| 2006/0241126 | A1 | 10/2006 | Hickey et al. |
| 2007/0123549 | A1 | 5/2007 | Hickey et al. |
| 2007/0155762 | A1 | 7/2007 | Leach et al. |
| 2008/0090851 | A1 | 4/2008 | Leach ..................... 514/264.1 |
| 2008/0090852 | A1 | 4/2008 | Leach ..................... 514/264.1 |

FOREIGN PATENT DOCUMENTS

| | | |
|---|---|---|
| WO | WO03/042206 | 5/2003 |
| WO | WO 03/087088 | 10/2003 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*

* cited by examiner

*Primary Examiner*—James O Wilson
*Assistant Examiner*—Douglas M Willis
(74) *Attorney, Agent, or Firm*—James M. Kanagy; Edward R. Gimmi; Charles M. Kinzig

(57) ABSTRACT

The invention disclosed herein relates to compounds of formula (I)

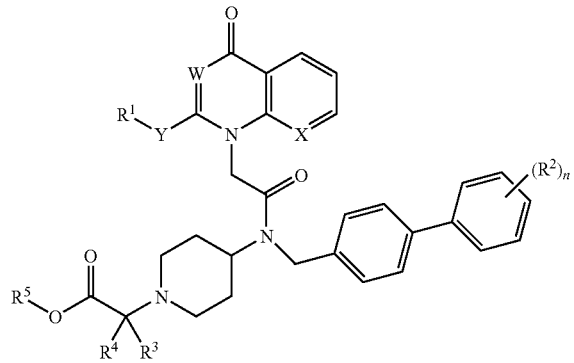

where the various groups are defined herein, and which are useful for treating inflammatory diseases such as atherosclerosis.

6 Claims, No Drawings

BICYCLIC HETEROAROMATIC COMPOUNDS

FIELD OF THE INVENTION

The present invention relates to certain novel quinazolines and naphthyridines, processes for their preparation, intermediates useful in their preparation, pharmaceutical compositions containing them, and their use in therapy, in particular in the treatment of atherosclerosis.

BACKGROUND OF THE INVENTION

WO 95/00649 (SmithKline Beecham plc) describes the phospholipase $A_2$ enzyme Lipoprotein Associated Phospholipase $A_2$ (Lp-$PLA_2$), the sequence, isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscler Thromb Vas Biol 1996:16;591-9) wherein it is referred to as LDL-$PLA_2$. A later patent application (WO 95/09921, Icos Corporation) and a related publication in Nature (Tjoelker et al, vol 374, 6 Apr. 1995, 549) describe the enzyme PAF-AH which has essentially the same sequence as Lp-$PLA_2$ and suggest that it may have potential as a therapeutic protein for regulating pathological inflammatory events.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, in particular having several pro-atherogenic activities ascribed to it including monocyte chemotaxis and induction of endothelial dysfunction, both of which facilitate monocyte-derived macrophage accumulation within the artery wall. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

A recently published study (WOSCOPS—Packard et al, N. Engl. J. Med. 343 (2000) 1148-1155) has shown that the level of the enzyme Lp-$PLA_2$ is an independent risk factor in coronary artery disease.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. An Lp-$PLA_2$ inhibitor could also find utility in other disease states that exhibit endothelial dysfunction including diabetes, hypertension, angina pectoris and after ischaemia and reperfusion.

Furthermore, Lp-$PLA_2$ inhibitors may also have a general application in any disorder that involves lipid oxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, ischaemia, reperfusion injury and acute and chronic inflammation.

In addition, Lp-$PLA_2$ inhibitors may also have a general application in any disorder that involves activated monocytes, macrophages or lymphocytes, as all of these cell types express Lp-$PLA_2$. Examples of such disorders include psoriasis.

Furthermore, Lp-$PLA_2$ inhibitors may also have a general application in any disorder that involves lipid oxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, ischaemia, reperfusion injury and acute and chronic inflammation.

Patent applications WO 01/60805, WO 02/30911, WO 02/30904, WO 03/016287, WO 03/042218, WO 03/042206, WO 03/041712, WO 03/086400, and WO 03/87088 disclose inhibitors of the enzyme Lp-$PLA_2$.

SUMMARY OF THE INVENTION

In a first aspect, this invention relates to a compound of formula (I)

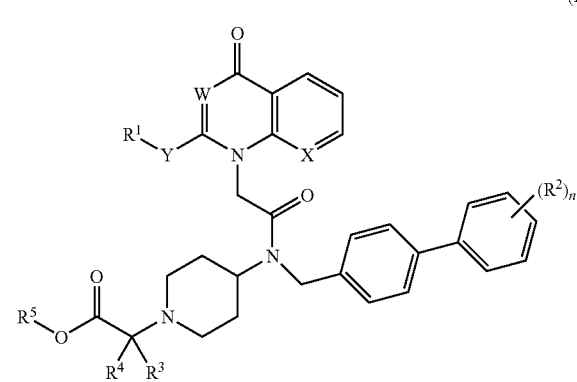

wherein:

$R^1$ is an aryl group, unsubstituted or substituted by 1, 2, 3 or 4 substituents which may be the same or different selected from the group consisting of $C_1$-$C_6$ alkyl, $C_1$-$C_6$ alkoxy, $C_1$-$C_6$ alkylthio, aryl $C_1$-$C_6$ alkoxy, hydroxy, halo, CN, $COR^6$, $COOR^6$, $NR^6COR^7$, $CONR^8R^9$, $SO_2NR^8R^9$, $NR^6SO_2R^7$, $NR^8R^9$, halo $C_1$-$C_4$ alkyl, and halo $C_1$-$C_4$ alkoxy;

W is CH and X is N, or W is N and X is CH, or W and X are both CH;

Y is $C_2$-$C_4$ alkyl, $R^2$ is $C_1$-$C_6$ alkyl, $C_1$-$C_6$ alkoxy, $C_1$-$C_6$ alkylthio, aryl $C_1$-$C_6$ alkoxy, hydroxy, halo, CN, $COR^6$, carboxy, $COOR^6$, $NR^6COR^7$, $CONR^8R^9$, $SO_2NR^8R^9$, $NR^6SO_2R^7$, $NR^8R^9$, mono to perfluoro-$C_1$-$C_6$ alkyl, or mono to perfluoro-$C_1$-$C_6$ alkoxy;

n is 0-5;

$R^3$ is $C_1$-$C_4$ alkyl;

$R^4$ is $C_1$-$C_4$ alkyl;

$R^5$ is hydrogen, $C_1$-$C_{10}$ alkyl, $C_2$-$C_{10}$ alkenyl, $C_2$-$C_{10}$ alkynyl, halo $C_1$-$C_4$ alkyl, $C_3$-$C_8$ cycloalkyl, $C_3$-$C_8$ cycloalkyl, $C_3$-$C_8$ cycloalkyl $C_1$-$C_4$ alkyl, $C_5$-$C_8$ cycloalkenyl, $C_5$-$C_8$ cycloalkenyl $C_1$-$C_4$ alkyl, 3-8-membered heterocycloalkyl, 3-8-membered heterocycloalkyl $C_1$-$C_4$ alkyl, $C_6$-$C_{14}$ aryl, $C_6$-$C_{14}$ aryl $C_1$-$C_{10}$ alkyl, heteroaryl, or heteroaryl $C_1$-$C_{10}$ alkyl; wherein each group is optionally one or more times by the same and/or a different group which is $C_1$-$C_6$ alkoxy, $C_1$-$C_6$ alkylthio, aryl $C_1$-$C_6$ alkoxy, hydroxy, halo, CN, $NR^8R^9$, or halo $C_1$-$C_4$ alkoxy $R^6$ and $R^7$ are independently hydrogen or $C_1$-$C_{10}$ alkyl;

$R^8$ and $R^9$ are the same or different and are hydrogen or $C_1$-$C_{10}$ alkyl, or $R^9$ and $R^{10}$ together with the nitrogen to which they are attached form a 5- to 7 membered ring optionally containing one or more further heteroatoms selected from oxygen, nitrogen and sulphur, and optionally substituted by one or two substituents selected from the group consisting of hydroxy, oxo, $C_1$-$C_4$ alkyl, $C_1$-$C_4$ alkylcarboxy, aryl, and aryl $C_1$-$C_4$ alkyl;

or a pharmaceutically acceptable salt thereof.

In another aspect, this invention relates to a pharmaceutical formulation comprising a compound of formula (I) or its salt and a pharmaceutically acceptable excipient.

In a further aspect, this invention encompasses a method for preventing or treating a disease in which inhibition of an enzyme characterized as being an Lp-PLA$_2$ enzyme will prevent, moderate or cure the disease, for example atherosclerosis, diabetes, rheumatoid arthritis, stroke, myocardial infarction, reperfusion injury, or acute and chronic inflammation.

The invention also relates to the use of a compound of formula (I) or its salt for manufacturing a medicament for preventing or treating diseases such as atherosclerosis diabetes, rheumatoid arthritis, stroke, myocardial infarction, reperfusion injury, or acute and chronic inflammation.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a compound of formula (I) or a salt thereof that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_4$-alkyl" and "$C_1$-$C_{10}$ alkyl" refers to an alkyl group having at least 1 and up to 4 or 10 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, n-octyl, n-nonyl, and n-decyl, and branched analogs of the latter 5 normal alkanes.

When the term "halo $C_1$-$C_4$ alkyl" is used it refers to an alkyl group having at least 1 and up to 4 carbon atoms that is substituted with at least one halogen selected from F, Cl, Br, and I on any or all of the carbons. Examples include, but are not limited to, fluoromethyl, difluoromethyl, trifluoromethyl, trichloromethyl, 2,2,2-trifluoroethyl, 2,2,2-trichloroethyl, pentafluoroethyl, 2-(trifluoromethyl)ethyl, and nonafluoro-tert-butyl.

When the term "halo $C_1$-$C_4$ alkoxy" is used it refers to an alkyl group having at least 1 and up to 4 carbon atoms that is substituted with at least one halogen selected from F, Cl, Br, and I on any or all of the carbons. Examples include, but are not limited to, fluoromethyl, difluoromethyl, trifluoromethyl, trichloromethyl, 2,2,2-trifluoroethyl, 2,2,2-trichloroethyl, pentafluoroethyl, 2-(trifluoromethyl)ethyl, and nonafluoro-tert-butyl.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

When "cycloalkyl" is used it refers to a non-aromatic, saturated, cyclic hydrocarbon ring containing the specified number of carbon atoms. So, for example, the term "$C_3$-$C_8$ cycloalkyl" refers to a non-aromatic cyclic hydrocarbon ring having from three to eight carbon atoms. Exemplary "$C_3$-$C_8$ cycloalkyl" groups useful in the present invention include, but are not limited to, cyclopropyl, cyclobutyl, cyclopentyl, cyclohexyl, cycloheptyl and cyclooctyl.

The term "$C_5$-$C_8$ cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where the phrase "a 3-8-membered heterocycloalkyl" is used, it means a non-aromatic heterocyclic ring containing the specified number of ring atoms being, saturated or having one or more degrees of unsaturation and containing one or more heteroatom substitutions selected from O, S and/or N. Such a ring may be optionally fused to one or more other "heterocyclic" ring(s) or cycloalkyl ring(s). Examples of "heterocyclic" moieties include, but are not limited to, aziridine, thiirane, oxirane, azetidine, oxetane, thietane, tetrahydrofuran, dihydropyran, tetrahydropyran, 1,4-dioxane, 1,3-dioxane, piperidine, piperazine, 2,4-piperazinedione, pyrrolidine, pyrroline, imidazolidine, pyrazolidine, pyrazoline, morpholine, thiomorpholine, tetrahydrothiopyrane, tetrahydrothiophene, and the like.

"Aryl" refers to monocyclic and polycarbocyclic unfused or fused groups having 6 to 14 carbon atoms and having at least one aromatic ring that complies with Hückel's Rule. Such a ring may be optionally fused to one or more other "heterocyclic" ring(s) or cycloalkyl ring(s). Examples of aryl groups are phenyl, biphenyl, naphthyl, anthracenyl, phenanthrenyl, 5,6,7,8-tetrahydronaphthalenyl, indenyl, fluorenyl, 2,3-dihydro-1,4-benzodioxinyl, 1,3-benzodioxolyl, 2,3-dihydro-1-benzofuranyl, 2,3-dihydro-1-benzothiophenyl, 2,3-dihydro-1H-indolyl, 2,3-dihydro-1H-benzimidazolyl, 2,3-dihydro-1H-benzoxazolyl, 2,3-dihydro-1H-benzothiazolyl, 3,4-dihydro-2H-1,4-benzoxazinyl, 3,4-dihydro-2H-1,4-benzothiazinyl, 1,2,3,4-tetrahydroquinolinyl, 1,2,3,4-tetrahydroquinoxalinyl, 3,4-dihydro-2H-1,4-chromenyl, 3,4-dihydro-2H-1,4-benzothiopyranyl and the like.

"Heteroaryl" means an aromatic monocyclic ring or polycarbocyclic fused ring system wherein at least one ring complies with Hückel's Rule, has the specified number of ring atoms, and that ring contains at least one heteroatom selected from N, O, and/or S. Examples of "heteroaryl" groups include furanyls, thiophenyls, pyrrolyls, imidazolyls, pyrazolyls, triazolyls, tetrazolyls, oxazolyls, isoxazolyls, oxadiazolyls, oxopyridyls, thiadiazolyls, thiazolyls, isothiazolyls, pyridinyls, pyridazinyls, pyrazinyls, pyrimidinyls, triazinyls, quinolinyls, quinoxalinyls, quinazolinyls, isoquinolinyls, cinnolinyls, naphthyridinyls, benzofuranyls, benzothiophenyls, benzimidazolyls, benzoxazolyls, benzothiazolyls, isoindolyls, indolyls, purinyls, indazolyls, and carbazolyls; and derivatives thereof.

The term "optionally" means that the subsequently described event(s) may or may not occur, and includes both event(s), which occur, and events that do not occur.

The term "solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Not withstanding the free base form of these compounds, some of which are crystalline, is of particular interest, salts are also included within the scope of the invention. Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to formula (I) may contain an acidic functional group, one acidic enough to form salts, for example when $R^5$ is hydrogen. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of formula (I) may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amophorus. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. Salts of particular interest include the L-tartrate, ethanedisulfonate (edisylate), sulfate, phosphate, p-toluenesulfonate (tosylate), along with other salts of interest which include the hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

Compounds of Particular Interest

Without intending to exclude any defined substituents and/or their recited radicals from the scope of this invention, the following R groups and the associated radicals are of particular interest:

As regards $R^1$, it may be an phenyl group optionally substituted by 1, 2, 3 or 4 substituents which may be the same or different selected from halo, $C_1$-$C_6$ alkyl, trifluoromethyl or $C_1$-$C_6$ alkoxy. More specifically, phenyl is unsubstituted or substituted by 1, 2, 3 or 4 halogen substituents, particularly, from 1 to 3 fluoro groups, and most particularly, 2,3-difluoro, 2,4-difluoro or 4-fluoro.

A further embodiment of formula (I) is where Y is —$CH_2CH_2$—.

The invention also provides a compound of formula (I) in which $R^2$ is hydrogen, by default, or is halo, $C_1$-$C_6$ alkyl, mono to perhalo-$C_1$-$C_4$ alkyl, mono to perhalo-C $C_1$—$C4_6$ alkoxy, or $C_1$-$C_6$ alkoxy; particularly mono to perfluoro-$C_1$-$C_4$ alkyl, mono to perfluoro-$C_1$-$C_4$ alkoxy, or $C_1$-$C_6$ alkoxy. Of particular interest are the compounds where $R^2$ is other than hydrogen, n in $(R^2)_n$ is 1, 2, or 3, and the substitution pattern is meta and/or para, particularly para, i.e. a 4-position substituent. Exemplified compounds include those where $R^2$ is 4-trifluoromethyl or 4-trifluoromethoxy.

$R^3$ and $R^4$ may be the same or different and are methyl, ethyl, n-propyl, or n-butyl. Of particular interest are those compounds of formula (I) where $R^3$ and $R^4$ are the same and are methyl, or ethyl; methyl is of particular interest.

$R^5$ may be hydrogen, $C_{(1-6)}$ alkyl which is a straight chain, or branched. Of particular interest is methyl, ethyl, propyl, isopropyl, n-butyl, sec-butyl, iso-butyl, t-butyl, n-pentyl or n-hexyl.

The compounds of formula (I) may be prepared in crystalline or non-crystalline form, and, if crystalline, may be solvated, e.g. as the hydrate. This invention includes within its scope stoichiometric solvates (e.g. hydrates).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the claimed compounds are included within the scope of the compounds of formula (I). The different isomeric forms may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

Where it is possible for compounds of formula (I) to exist in one or more tautomeric forms, all such tautomers and mixtures thereof are included in the scope of the invention.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like. Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number (such as two, three, four, five or six) of sub-doses per day such that the total daily dose is the same or intermittently, such as once every other day. An effective amount of a salt or solvate, etc., may be determined as a proportion of the effective amount of the compound of formula (I) per se. It is envisaged that similar dosages would be appropriate for treatment of the other conditions referred to above.

General Purification and Analytical Methods

Preparative HPLC was conducted on a Gilson instrument with a Xterra Prep MS $C_{18}$ 5.0 µm column (50 mm×50 mm, i.d.) by the following methods:
A) eluting with $NH_4OH$ (pH=10)/$CH_3CN$ 45% to 90%, over a 15 minutes gradient with a flow rate of 84 ml/min.
B) eluting with $NH_4OH$ (pH=10)/$CH_3CN$ 40% to 90%, over a 15 minutes gradient with a flow rate of 84 ml/min.

Analytical LCMS was conducted on an Agilent 1100 Series LC/MSD SL or VL using electrospray positive [ES+ve to give $MH^+$] equipped with a Sunfire $C_{18}$ 5.0 µm column (3.0 mm×50 mm, i.d.), eluting with 0.05% TFA in water (solvent A) and 0.05% TFA in acetonitrile (solvent B), using the following elution gradient 10%-99% (solvent B) over 3.0 minutes and holding at 99% for 1.0 minutes at a flow rate of 1.0 ml/minutes.

$^1$H-NMR spectra were recorded using a Bruker Avance 400 MHz spectrometer. Assignment of spectra for Examples 1-7 was typically complicated by the presence of a mixture of rotamers about the amide bond, leading to peak doubling and non-integer peak integrals. For the most ambiguous cases only partial spectra are listed.

Abbreviations

The following abbreviations are used herein:

$CDCl_3$ deuterated chloroform
$CD_3OD$ deuterated methanol
DCE 1,2-dichloroethane
DCM dichloromethane
DIPEA diisopropylethylamine
DMF N,N-dimethylformamide
DMSO dimethylsulfoxide
$d_6$-DMSO deuterated dimethylsulfoxide
ES+ MS Positive Electrospray mass spectrometry
h hours
ES− MS Negative Electrospray mass spectrometry
HATU O-(7-azabenzotriazol-1-yl)-N,N,N',N'-tetramethyluronium hexafluorophosphate
HPLC high pressure liquid chromatography
LCMS Liquid Chromatography Mass Spectrometry min minutes
NMR Nuclear Magnetic Resonance spectroscopy
Rt retention time
RT room temperature
TFA trifluoroacetic acid Nomenclature Intermediates and Examples were named using ACD/Name version 6.02 (Advanced Chemistry Development, Inc., [ACD/Labs] Toronto, Canada; http://www.acdlabs.com/products/name_lab/name/.)

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

Synthetic Route

The following flow chart illustrates a process for making the compounds of this invention.

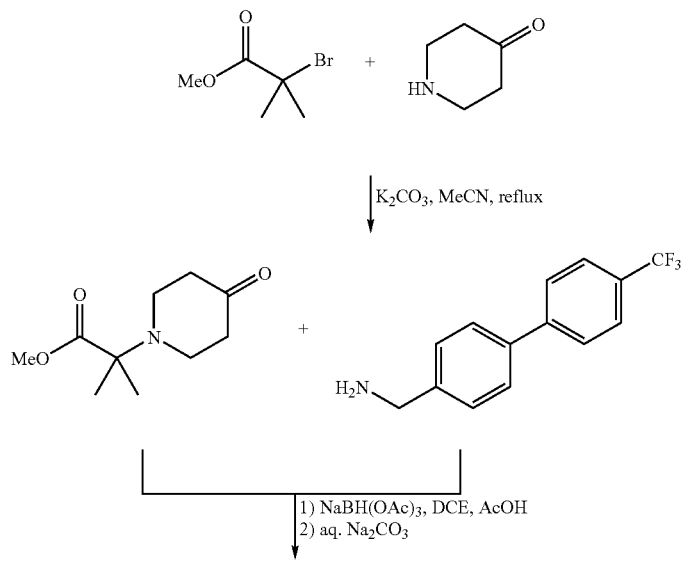

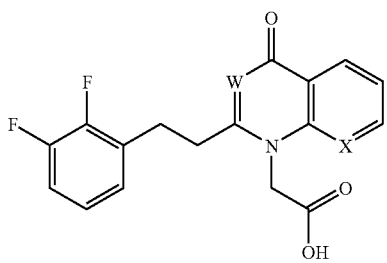 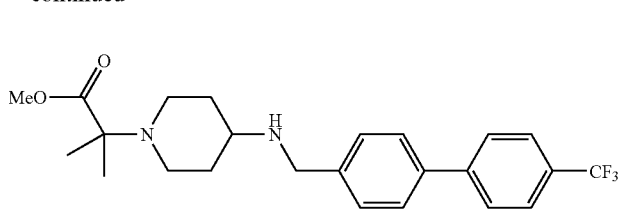

|HATU, DIPEA, DMF

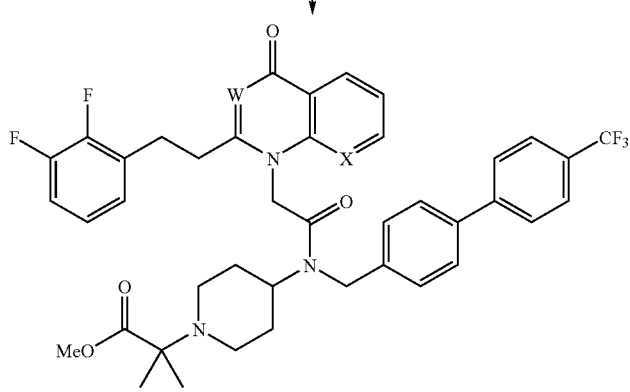

In addition, the reader is referred to published PCT application WO 03/016287 for chemistries that may be useful in preparing some of the intermediates set out in this flow chart. Those chemistries, to the extent they are useful in this case, are incorporated herein by reference as though it was fully set out herein. In addition, reference is made to the syntheses set out in published PCT applications WO 01/60805, WO 02/30911, WO 02/30904, WO 03/042218, WO 03/042206, WO 03/041712, WO 03/086400, and WO 03/87088, noted above. To the extent the reader wishes to prepare the instant compounds by using intermediates, reagents, solvents, times, temperatures, etc., other than those in the route on the foregoing page, these published PCT applications may provide useful guidance. To the extent the chemistries in these PCT applications are pertinent to making the instant compounds, those materials are incorporated herein by reference.

Specific Examples

Intermediate A1

{[4'-(Trifluoromethyl)-4-biphenylyl]methyl} amine

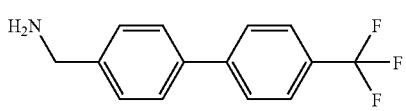

The preparation of this compound was described in WO 02/30911 as Intermediate D7.

Intermediate A2

({4'-[(Trifluoromethyl)oxy]-4-biphenylyl}methyl) amine hydrochloride

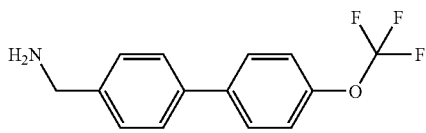

A solution of 4'-[(trifluoromethyl)oxy]-4-biphenylcarbonitrile (prepared from {4-[(trifluoromethyl)oxy]phenyl}boronic acid by a method analogous to that described for the 4'-trifluoromethyl analogue, Intermediate D6 of WO 02/30911) (66.6 g) in ethanol (2000 ml) and concentrated hydrochloric acid (100 ml) was hydrogenated over Pearlman's catalyst (10 g) at 25 psi until reduction was complete. The catalyst was removed by filtration through celite, then the solvent was removed in vacuo to obtain the desired product.

LCMS Rt=2.212 minutes; m/z [M+H]$^+$=251.0

Intermediate A3

Methyl 2-methyl-2-(4-oxo-1-piperidinyl)propanoate

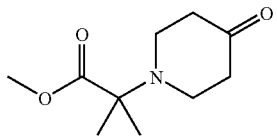

A mixture of methyl 2-bromo-2-methylpropanoate (80.87 ml, 5 equiv), 4-piperidone hydrochloride monohydrate (19.6 g, 1 equiv), acetonitrile (200 ml) and potassium carbonate (69.1 g, 4 equiv) was heated at reflux under nitrogen with mechanical stirring for 17.5 h then cooled in an ice bath before adding diethyl ether (100 ml). Filtration through celite followed by flash chromatography (silica, 10-50% ethyl acetate in hexane) and evaporation of the product fractions gave the desired product as a yellow oil (14.28 g).

$^1$H NMR (CDCl$_3$) δ 1.41 (6H,s), 2.47 (4H,m), 2.88 (4H,m), 3.73 (3H,s).

Intermediate A4

Ethyl 2-methyl-2-(4-oxo-1-piperidinyl)propanoate

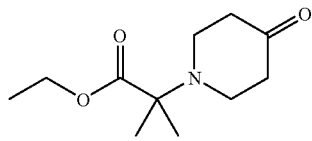

A mixture of ethyl 2-bromo-2-methylpropanoate (48.3 ml, 5 equiv), 4-piperidone hydrochloride monohydrate (100 g, 1 equiv), acetonitrile (1216 ml) and potassium carbonate (353 g, 4 equiv) was heated at reflux under nitrogen with mechanical stirring for 20 h then cooled in an ice bath before adding diethyl ether (approx. 1400 ml). The mixture was filtered through celite, evaporated in vacuo, then excess bromoester distilled off (50° C. still head temperature/10 Torr). Flash chromatography (silica, 5-30% ethyl acetate in hexane) and evaporation of the product fractions gave the crude product as a yellow oil. To remove some remaining bromoester contaminant this was partitioned between ethyl acetate and 2M aqueous hydrochloric acid. The organic layer was discarded and the aqueous layer was basified with sodium carbonate, saturated with sodium chloride and extracted with ethyl acetate. Drying and evaporation of the organic extracts gave the desired product as a yellow oil (54.7 g).

$^1$H NMR (CDCl$_3$) δ 1.27 (3H,t), 1.40 (6H,s), 2.47 (4H,m), 2.90 (4H,m), 4.20 (2H,q).

Intermediate A5

1,1-Dimethylethyl 2-methyl-2-(4-oxo-1-piperidinyl)propanoate

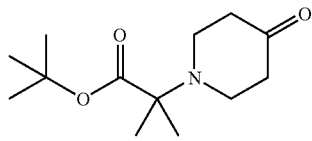

A mixture of 1,1-dimethylethyl 2-bromo-2-methylpropanoate (8.0 g, 1.1 equiv), 4-piperidone hydrochloride (5.0 g, 1 equiv), acetone (50 ml) and potassium carbonate (13.0 g, 3 equiv) was heated at reflux with stirring for 24 h, then filtered and the filtrate evaporated.

The crude residue was used in the next step without purification.

ES+MS m/z [M+H-tBu]$^+$=186.1

Intermediate B1

Methyl 2-methyl-2-[4-({[4'-(trifluoromethyl)-4-biphenylyl]methyl}amino)-1-piperidinyl]propanoate

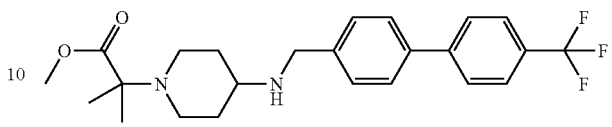

A mixture of methyl 2-methyl-2-(4-oxo-1-piperidinyl) propanoate (Int. A3) (14.28 g, 1 equiv), {[4'-(trifluoromethyl)-4-biphenylyl]methyl}amine (Int. A1) (19.6 g, 0.85 equiv), DCE (300 ml), acetic acid (3.8 ml, 0.90 equiv) and sodium triacetoxyborohydride (20.7 g, 1.25 equiv) was stirred at room temperature under nitrogen for 17.5 h. Aqueous sodium carbonate (2M solution, excess) was added and stirred for 4 h, then the mixture was extracted with a mixture of diethyl ether and THF. The organic extracts were backwashed with water and brine, dried over sodium sulfate and filtered through a pad of silica gel which was rinsed with 2.5% methanol in DCM. After evaporation in vacuo, the crude product was crystallised from ether/hexane, finally at ice bath temperature, which after drying yielded a white solid (20.9 g).

LCMS Rt=2.070 minutes; m/z [M+H]$^+$=435.2 $^1$H NMR (d$_6$-DMSO) δ 1.15-1.32 (8H, m), 1.75-187(2H,m), 1.97-2.12 (2H,m), 2.27-2.40 (1H, m), 2.77-2.90(2H,m), 3.60 (3H,s), 3.76 (2H,s), 7.46 (2H, d, J=8.03 Hz), 7.67 (2H, d, J=8.28 Hz), 7.80 (2H, d, J=8.53 Hz), 7.88 (2H, d, 8.03 Hz)

Intermediate B2

Ethyl 2-methyl-2-[4-({[4'-(trifluoromethyl)-4-biphenylyl]methyl}amino)-1-piperidinyl]propanoate

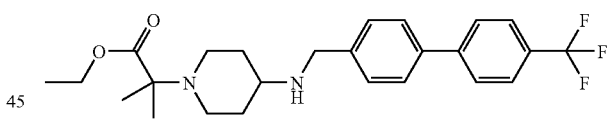

A mixture of ethyl 2-methyl-2-(4-oxo-1-piperidinyl)propanoate (Int. A4) (25.6 g, 1.2 equiv), {[4'-(trifluoromethyl)-4-biphenylyl]methyl}amine (Int. A1) (31.1 g, 1.0 equiv), DCE (400 ml) and acetic acid (6.3 ml, 1.1 equiv) was stirred at room temperature under nitrogen. Sodium triacetoxyborohydride (33.5 g, 1.5 equiv) was added and stirring continued for 19 hours. Aqueous sodium carbonate (2M solution, excess) was added and stirred for 1.5 h, then the mixture was extracted with a mixture of diethyl ether and THF. The organic extracts were backwashed with water and brine, filtered through a pad of silica gel, dried over sodium sulfate and evaporated in vacuo. The desired product was obtained as a white solid (44.2 g) which was used without further purification.

LCMS Rt=2.194 minutes; m/z [M+H]$^+$=449.3 $^1$H NMR (d$_6$-DMSO) δ 1.06-1.32 (1H,m), 1.74-1.89 (2H,m), 1.99-2.14 (2H, m), 2.25-2.39 (1H, m), 2.69-2.89 (2H, m), 3.75 (2H, s), 4.01-4.12 (2H, m), 7.45 (2H, d, J=7.55 Hz), 7.67 (2H, d, J=7.81 Hz), 7.79 (2H, d, J=8.06 Hz), 7.88 (2H, d, J=8.06 Hz)

Intermediate B3

Ethyl 2-methyl-2-{4-[({4'-[(trifluoromethyl)oxy]-4-biphenylyl}methyl)amino]-1-piperidinyl}propanoate

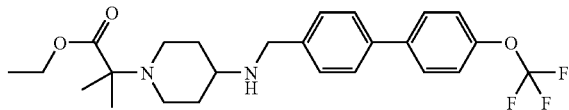

A mixture of ethyl 2-methyl-2-(4-oxo-1-piperidinyl)propanoate (Int. A4) (1.09 g, 1.2 equiv), ({4'-[(trifluoromethyl)oxy]-4-biphenylyl}methyl)amine hydrochloride (Int. A2) (1.28 g, 1.0 equiv), DCE (21 ml) and acetic acid (0.27 ml, 1.1 equiv) was stirred at room temperature under nitrogen. Sodium triacetoxyborohydride (1.42 g, 1.5 equiv) was added and stirring continued for 3 hours. Aqueous sodium carbonate (2M solution, excess) was added and stirred for 45 min, then the mixture was partitioned with a mixture of diethyl ether/THF and water. The organic extracts were backwashed with water and brine, and dried over sodium sulfate and evaporated in vacuo. The desired product was obtained as a light yellow solid (2.14 g) which was used without further purification.

LCMS Rt=2.244 minutes; m/z [M+H]$^+$=465.3

Intermediate B4

1,1-Dimethylethyl 2-methyl-2-[4-({[4'-(trifluoromethyl)-4-biphenylyl]methyl}amino)-1-piperidinyl]propanoate

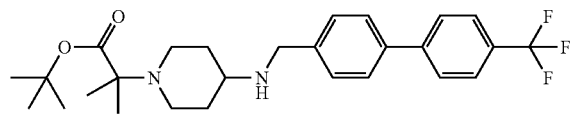

A mixture of 1,1-dimethylethyl 2-methyl-2-(4-oxo-1-piperidinyl)propanoate (Int. A6) (370 mg, 1.2 equiv), {[4'-(trifluoromethyl)-4-biphenylyl]methyl}amine (Int. A1) (397 mg, 1 equiv), sodium triacetoxyborohydride (400 mg, 1.5 equiv), DCM (10 ml) and acetic acid (0.076 ml, 1 equiv) was combined and stirred at room temperature until LCMS confirmed disappearance of the amine starting material (approx. 18 hours). Aqueous sodium carbonate was added and then extracted with DCM. The organics were dried over sodium sulfate and concentrated to give a solid (420 mg) that was used without further purification.

LCMS Rt=2.24 minutes; m/z [M+H]$^+$=477.3

Intermediate C1

[2-[2-(2,3-Difluorophenyl)ethyl]-4-oxo-1 (4H)-quinazolinyl]acetic acid

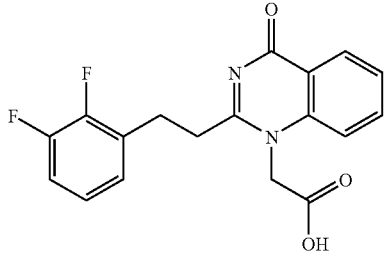

The preparation of this compound was described in WO 02/30911 as Intermediate C43.

Intermediate C2

[2-[2-(2,3-Difluorophenyl)ethyl]-4-oxo-1,8-naphthyridin-1 (4H)-yl]acetic acid

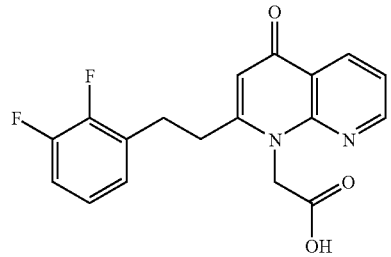

The preparation of this compound was described in WO 02/30904 as Intermediate E21.

Intermediate C3

[2-[2-(2,4-Difluorophenyl)ethyl]-4-oxo-1(4H)-quinazolinyl]acetic acid

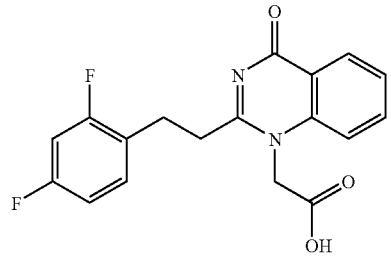

The preparation of this compound was described in WO 02/30911 as Intermediate C45.

Example 1

Methyl 2-[4-({[2-[2-(2,3-difluorophenyl)ethyl]-4-oxo-1 (4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

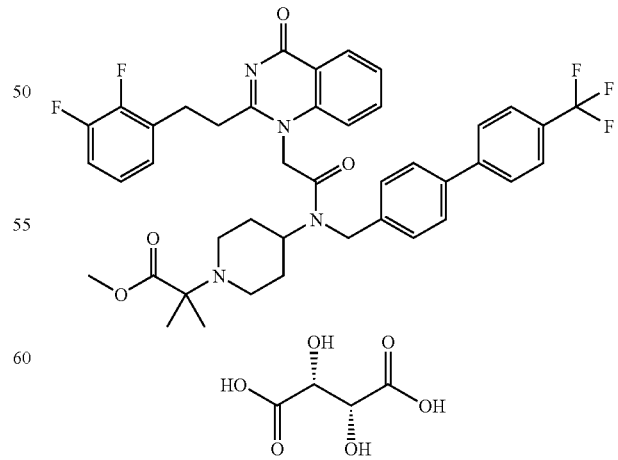

A mixture of [2-[2-(2,3-difluorophenyl)ethyl]-4-oxo-1 (4H)-quinazolinyl]acetic acid (Int. C1) (100 mg, 1 equiv), methyl 2-methyl-2-[4-({[4'-(trifluoromethyl)-4-biphenylyl]methyl}amino)-1-piperidinyl]propanoate (Int. B1) (130 mg, 1.03 equiv), DIPEA (0.1 ml, 3.6 equiv), acetonitrile (2 ml) and HATU (130 mg, 1.4 equiv) was stirred at room temperature for 1 h, then evaporated and redissolved in acetonitrile. Purification by reverse phase HPLC (Preparative Method A) gave methyl 2-[4-({[2-[2-(2,3-difluoro-phenyl)ethyl]-4-oxo-1(4H)-quinazolinyl]acetyl} {[4'-(trifluoromethyl)-4-biphenylyl]-methyl}amino)-1-piperidinyl]-2-methylpropanoate (128 mg).

LCMS Rt=2.686 minutes; m/z [M+H]$^+$=761.3 $^1$H NMR (CDCl$_3$) δ 1.33 (3H, s), 1.36 (3H, s), 1.83-2.02 (4H, m), 2.36-2.48 (2H, m), 2.87-2.91 (1H, m), 3.06-3.09 (2H, m), 3.16-3.20 (2H, m), 3.26-3.29 (1H, m), 3.71-3.73 (3H, m), 4.02/4.51 (1H, 2×br m), 4.74 (1H, s), 4.92 (1H, s), 5.12 (1H, s), 5.56 (1H, s), 7.00-7.19 (3H, m), 7.32-7.37 (1H, m), 7.48-7.62 (5H, m), 7.72-7.81 (5H, m), 8.22-8.28 (1H, m).

The free base was converted to the bitartrate salt by adding L-tartaric acid (1.675 g, 1.0 equiv) in one portion and stirred for 30 minutes at room temperature. The solution was concentrated in vacuo to an off-white powder that was dried in a vacuum oven at room temperature.

Example 2

Methyl 2-[4-({[2-[2-(2,3-difluorophenyl)ethyl]-4-oxo-1,8-naphthyridin-1(4H)-yl]acetyl}-{[4'-(trifluoromethyl)-4-biphenylyl]methyl}amino)-1-piperidinyl]-2-methylpropanoate 2,3-dihydroxybutanedioate (salt)

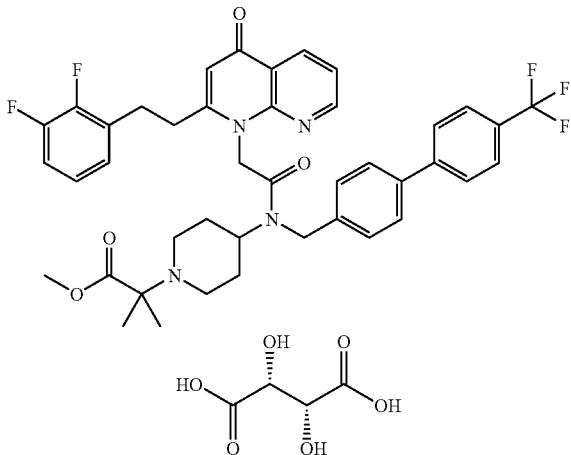

A mixture of [2-[2-(2,3-difluorophenyl)ethyl]-4-oxo-1,8-naphthyridin-1(4H)-yl]acetic acid (Int. C2) (100 mg, 1 equiv), carbonyldiimidazole (50 mg, 1.05 equiv) and dimethyl-acetamide (4 ml) was stirred at 60° C. for 30 min then methyl 2-methyl-2-[4-({[4'-(trifluoro-methyl)-4-biphenylyl]methyl}amino)-1-piperidinyl]propanoate (Int. B1) (132 mg, 1.05 equiv) was added and the temperature raised to 80° C. for 2 h. A further portion of carbonyldiimidazole (0.5 equiv) was added and stirring continued at 80° C. for 15 h. After cooling the crude mixture was applied to reverse phase HPLC (Preparative Method A) to obtain methyl 2-[4-({[2-[2-(2,3-difluorophenyl)ethyl]-4-oxo-1,8-naphthyridin-1(4H)-yl]-acetyl} {[4'-(trifluoromethyl)-4-biphenylyl]methyl}amino)-1-piperidinyl]-2-methyl-propanoate (99 mg).

LCMS Rt=2.845 minutes; m/z [M+H]+=761.3 1H NMR (CDCl$_3$) δ 1.28 (3H, s), 1.31 (3H, s), 1.73-2.05 (4H, m), 2.25 (1H, t), 2.39-2.46 (1H, m), 2.96-2.99 (1H, m), 3.00-3.12 (4H, m), 3.19 (1H, s), 3.68-3.73 (3H, m), 4.11/4.41 (1H, 2×br m), 4.73 (1H, s), 4.97 (1H, s), 5.51 (1H, s), 6.29-6.34 (1H, m), 7.06-7.20 (2H, m), 7.35-7.41 (1H, m), 7.48-7.58 (2H, m), 7.68-7.84 (6H, m), 8.60-8.68 (1H, m), 8.87-8.91 (1H, m).

This was converted to the bitartrate salt by a method analogous to that described for Example 1.

Example 3

Ethyl 2-[4-({[2-[2-(2,3-difluorophenyl)ethyl]-4-oxo-1(4H)-quinazolinyl]acetyl} {[4'-(trifluoromethyl)-4-biphenylyl]methyl}amino)-1-piperidinyl]-2-methyl-propanoate 2,3-dihydroxybutanedioate (salt)

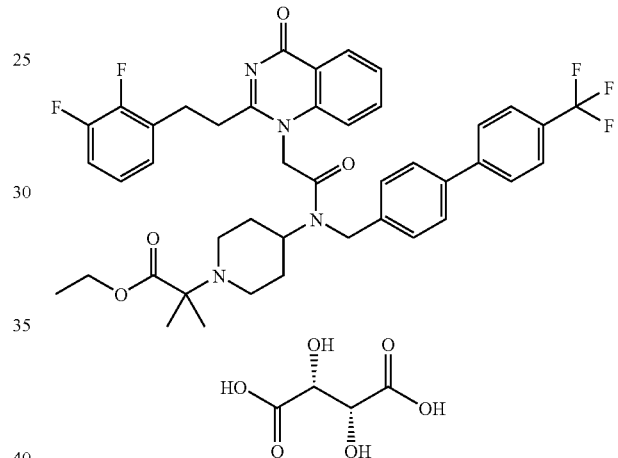

A mixture of [2-[2-(2,3-difluorophenyl)ethyl]-4-oxo-1(4H)-quinazolinyl]acetic acid (Int. C1) (115 mg, 1 equiv), ethyl 2-methyl-2-[4-({[4'-(trifluoromethyl)-4-biphenylyl]methyl}amino)-1-piperidinyl]propanoate (Int. B2) (150 mg, 1 equiv), HATU (151 mg, 1.2 equiv), DMF (2.7 ml) and DIPEA (0.17 ml, 3 equiv) was shaken at room temperature for 5 h. The reaction mixture was partitioned between ethyl acetate/methanol and aqueous sodium bicarbonate, then the organic layer was brine-washed and dried. Flash chromatography (silica, 3-4% methanol in DCM) gave ethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate as a white solid (190 mg).

LCMS Rt=2.55 minutes; m/z [M+H]+=775.3 $^1$H NMR (CDCl$_3$) δ 1.18-1.40 (9H, m), 1.61-2.09 (4H, m), 2.22-2.45 (2H, m), 2.75-2.85 (1H, m), 2.90-3.34 (5H, m), 3.71/4.66 (1H, 2×m), 4.12-4.26 (2H, m), 4.70-4.85 (3H, m), 5.08 (1H, s), 6.80-6.88 (1H,m), 6.95-7.13 (3H, m), 7.27-7.33 (1H, m), 7.34-7.52 (3H,m), 7.56-7.62 (1H, m), 7.63-7.77 (4H, m), 8.29-8.44 (2H, m).

This was converted to the bitartrate salt by a method analogous to that described in Example 1.

Example 4

Ethyl 2-{4-[{[2-[2-(2,3-difluorophenyl)ethyl]-4-oxo-1(4H)-quinazolinyl]acetyl} ({4'-[(trifluoromethyl)oxy]-4-biphenylyl}methyl)amino]-1-piperidinyl}-2-methylpropanoate 2,3-dihydroxybutanedioate (salt)

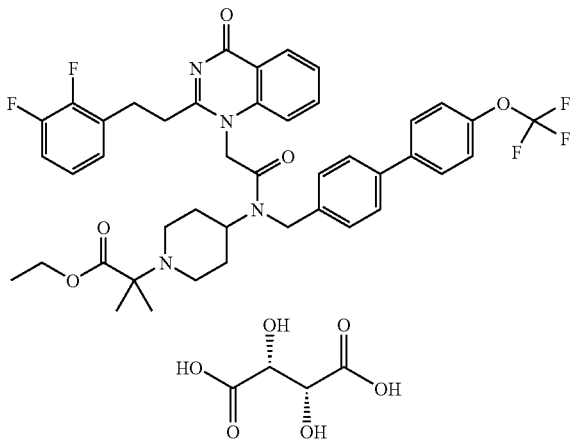

A mixture of [2-[2-(2,3-difluorophenyl)ethyl]-4-oxo-1(4H)-quinazolinyl]acetic acid (Int. C1) (124 mg, 1.2 equiv), ethyl 2-methyl-2-{4-[({4'-[(trifluoromethyl)oxy]-4-biphenylyl}methyl)amino]-1-piperidinyl}propanoate (Int. B3) (139 mg, 1 equiv), DMF (1.2 ml) and DIPEA (0.16 ml, 3 equiv) was shaken at room temperature for 30 min, then HATU (176 mg, 1.5 equiv) was added and shaking continued for 4 h. Reverse phase HPLC (Preparative Method B) gave ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate as a white solid (174 mg).

LCMS Rt=2.77 minutes; m/z [M+H]$^+$=791.3 $^1$H NMR (CDCl$_3$) Characteristic peaks: δ 1.21-1.42 (9H, m), 1.58-2.08 (4H, m), 2.20-2.48 (2H, m), 2.71-5.1 (13H, br m), 6.79-6.87 (1H, d), 6.92-7.11 (3H, m), 7.30-7.46 (5H, m), 7.48-7.63 (5H, m), 8.26-8.40 (1H, m)

This was converted to the bitartrate salt by a method analogous to that described in Example 1.

Example 5

Methyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate 2,3-dihydroxybutanedioate (salt)

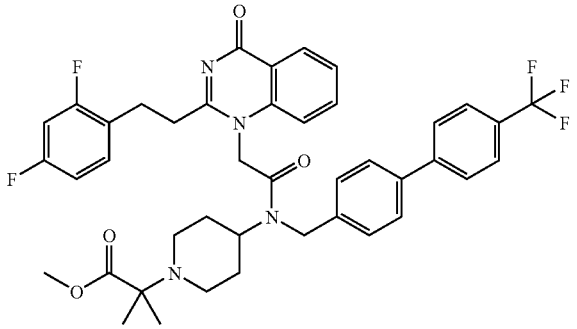

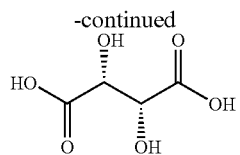

A mixture of [2-[2-(2,4-difluorophenyl)ethyl]-4-oxo-1(4H)-quinazolinyl]acetic acid (Int. C3) (100 mg, 1 equiv), methyl 2-methyl-2-[4-({[4'-(trifluoromethyl)-4-biphenylyl]methyl}amino)-1-piperidinyl]propanoate (Int. B1) (130 mg, 1.03 equiv), DIPEA (0.1 ml, 2 equiv), acetonitrile (2 ml) and HATU (130 mg, 1.4 equiv) was stirred at room temperature for 1 h, then evaporated and redissolved in acetonitrile. Purification by reverse phase HPLC (Preparative Method B) gave methyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate (126 mg).

LCMS Rt=2.698 minutes; m/z [M+H]$^+$=761.3 $^1$H NMR (CDCl$_3$) δ 1.30 (3H, s), 1.34 (3H s), 1.81-2.03 (4H, m), 2.29-2.35 (1H, m), 2.39-2.45 (1H, m), 2.82-2.87 (1H, m), 3.00-3.14 (4H, m), 3.19-3.24 (1H, m), 3.70-3.73 (3H, m), 4.00/4.51 (1H, 2×br m), 4.74 (1H, s), 4.91 (1H, s), 5.10 (1H, s), 5.54 (1H, s), 6.77-6.84 (1H, m), 6.87-6.98 (1H, m), 7.28-7.43 (2H, m), 7.48-7.61 (5H, m), 7.73-7.81 (5H, m), 8.23-8.29 (1H, m).

This was converted to the bitartrate salt by a method analogous to that described in Example 1.

Example 6

Ethyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate 2,3-dihydroxybutanedioate (salt)

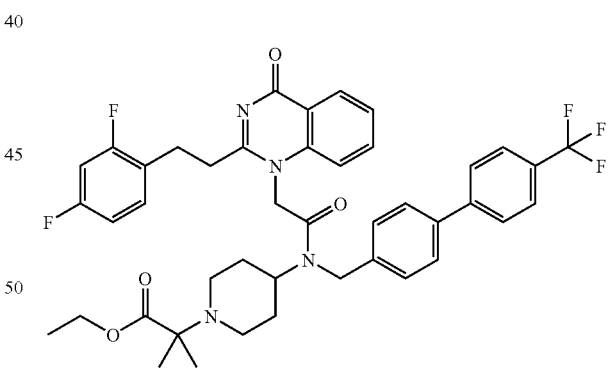

A mixture of [2-[2-(2,4-difluorophenyl)ethyl]-4-oxo-1(4H)-quinazolinyl]acetic acid (Int. C3) (120 mg, 1 equiv), ethyl 2-methyl-2-[4-({[4'-(trifluoromethyl)-4-biphenylyl]methyl}-amino)-1-piperidinyl]propanoate (Int. B2) (204 mg, 1.3 equiv), DMF (1.4 ml) and DIPEA (0.183 ml, 3 equiv) was shaken at room temperature, then HATU (206 mg, 1.5 equiv) was added with vigorous agitation and shaking continued for 1.5 h. A further portion of Intermediate D5 (12 mg, 0.1 equiv)

was added then shaking was continued for 2 days. Reverse phase HPLC (Preparative Method B) gave ethyl 2-[4-({[2-[2-(2,4-difluorophenyl)ethyl]-4-oxo-1(4H)-quinazolinyl] acetyl} {[4'-(trifluoromethyl)-4-biphenylyl]methyl}amino)-1-piperidinyl]-2-methylpropanoate as a white solid (173 mg).

LCMS Rt=2.751 minutes; m/z [M+H]+=775.3 ¹H NMR (CDCl₃)δ(mixture of rotomers) Characteristic peaks: 1.22-1.47 (9H, m), 1.63-2.10 (4H, m), 2.16-5.11 (15H, br m), 6.75-6.88 (2H, m), 7.14-7.80 (12H, m), 8.26-8.40 (1H, m).

This was converted to the bitartrate salt by a method analogous to that described in Example 1.

Example 7

Ethyl 2-{4-[{[2-[2-(2,4-difluorophenyl)ethyl]-4-oxo-1(4H)-quinazolinyl]acetyl} ({4'-[(trifluoromethyl)oxy]-4-biphenylyl}methyl)amino]-1-piperidinyl}-2-methylpropanoate 2,3-dihydroxybutanedioate (salt)

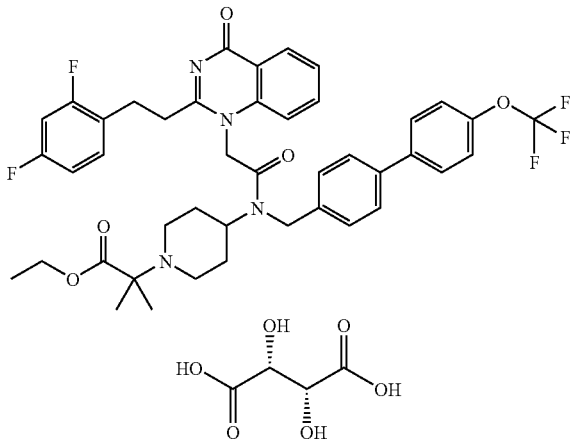

A mixture of [2-[2-(2,4-difluorophenyl)ethyl]-4-oxo-1 (4H)-quinazolinyl]acetic acid (Int. C3) (114 mg, 1.1 equiv), ethyl 2-methyl-2-{4-[({4'-[(trifluoromethyl)oxy]-4-biphenylyl}methyl)amino]-1-piperidinyl}propanoate (Int. B3) (139 mg, 1 equiv), DMF (1.2 ml) and DIPEA (0.16 ml, 3 equiv) was shaken at room temperature, then HATU (176 mg, 1.5 equiv) was added with vigorous agitation and shaking continued for 30 min. A further portion of Intermediate D5 (21 mg, 0.2 equiv) was added, followed 1 h later by further HATU (23 mg, 0.2 equiv), then shaking was continued for 18 h. Reverse phase HPLC (Preparative Method B) gave ethyl 2-{4-[{[2-[2-(2,4-difluorophenyl)ethyl]-4-oxo-1(4H)-quinazolinyl]acetyl} ({4'-[(trifluoromethyl)oxy]-4-biphenylyl}methyl)amino]-1-piperidinyl}-2-methylpropanoate as a white solid (149 mg).

LCMS Rt=2.793 minutes; m/z [M+H]+=791.3 ¹H NMR (CDCl₃) Characteristic peaks: δ 1.20-1.45 (9H, m), 1.58-2.12 (4H, m), 2.14-2.48 (2H,m), 2.620-5.11 (1H, m), 6.59-6.72 (1H, m), 6.73-6.90 (2H, m), 7.16-7.64 (11H. m), 8.25-8.40 (1H, m).

This was converted to the bitartrate salt by a method analogous to that described in Example 2.

Example 8

2-[4-({[2-[2-(2,3-Difluorophenyl)ethyl]-4-oxo-1,8-naphthyridin-1(4H)-yl]acetyl} {[4'-(trifluoromethyl)-4-biphenylyl]methyl}amino)-1-piperidinyl]-2-methylpropanoic acid trifluoroacetate

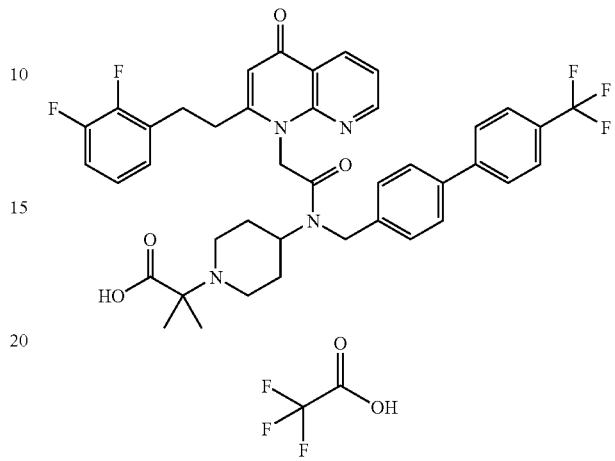

A mixture of 1,1-dimethylethyl 2-methyl-2-[4-({[4'-(trifluoromethyl)-4-biphenylyl]methyl}amino)-1-piperidinyl] propanoate (Int. B4) (1 equiv), [2-[2-(2,3-difluorophenyl) ethyl]-4-oxo-1,8-naphthyridin-1(4H)-yl]acetic acid (Int. C2) (1.2 equiv), DIPEA (3 equiv) and DMF (1.0 ml) is stirred at room temperature for 5 min. HATU (1.5 equiv) is added in 1 portion and stirred an additional 5 min. The crude reaction mixture is concentrated, filtered through a plug of silica eluted with acetone and evaporated to obtain crude 1,1-dimethylethyl 2-[4-({[2-[2-(2,3-difluorophenyl)ethyl]-4-oxo-1, 8-naphthyridin-1(4H)-yl]acetyl} {[4'-(trifluoromethyl)-4-biphenylyl]methyl}amino)-1-piperidinyl]-2-methyl propanoate.

The proponate, without isolation, is dissolved in a 1:1 mixture of TFA and DCM and stirred at RT for 4 h. Evaporation and prepative HPLC (Method A) gives the captioned compound.

Other salts can be prepared by conventional means. The free base can also be prepared by conventional means.

Example 9

2-[4-({[2-[2-(2,3-Difluorophenyl)ethyl]-4-oxo-1 (4H)-quinazolinyl]acetyl} {[4'-(trifluoromethyl)-4-biphenylyl]methyl}amino)-1-piperidinyl]-2-methyl-propanoic acid trifluoroacetate

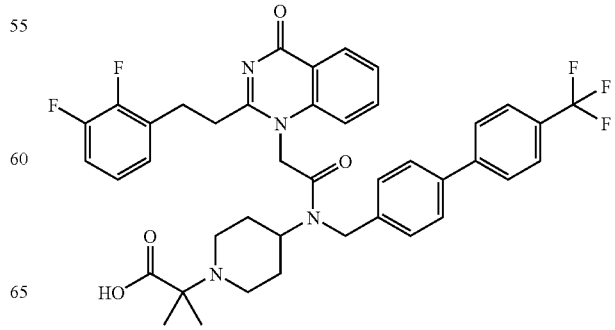

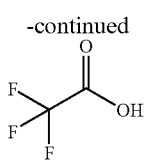

A mixture of 1,1-dimethylethyl 2-methyl-2-[4-({[4'-(trifluoromethyl)-4-biphenylyl]methyl}amino)-1-piperidinyl] propanoate (Int. B4) (1 equiv), [2-[2-(2,3-difluorophenyl) ethyl]-4-oxo-1(4H)-quinazolinyl]acetic acid (Int. C1) (1.2 equiv), DIPEA (3 equiv) and DMF (1.0 ml) is stirred at room temperature for 5 min. HATU (1.5 equiv) is added in 1 portion and stirred an additional 5 min. The crude reaction mixture is concentrated, filtered through a plug of silica eluted with acetone and evaporated to obtain crude 1,1-dimethylethyl 2-[4-({[2-[2-(2,3-difluorophenyl)ethyl]-4-oxo-1(4H)-quinazolinyl]acetyl} {[4'-(trifluoromethyl)-4-biphenylyl] methyl}amino)-1-piperidinyl]-2-methylpropanoate.

The proponate, without isolation, is dissolved in a 1:1 mixture of TFA and DCM and stirred at RT for 4 h. Evaporation and prepative HPLC (Method A) gives the captioned compound.

Other salts can be prepared by conventional means. The free base can also be prepared by conventional means.

Biological Data

1) Screen for Lp-PLA₂ Inhibition

Recombinant Lp-PLA₂ was purified to homogeneity from baculovirus infected Sf9 cells, using a zinc chelating column, blue sepharose affinity chromatography and an anion exchange column. Following purification and ultrafiltration, the enzyme was stored at 6 mg/ml at 4° C. Assay buffer was composed of Tris-HCl (50 mM), NaCl (150 mM) and 1 mM CHAPS, pH 7.4 at room temperature. Activity was measured by an increase in emission at 535 nm on hydrolysis of N-((6-(2,4-dinitrophenyl)amino)hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6, Molecular Probes catalogue reference D-23739) as substrate, using a fluorometric plate reader with 384 well microtitre plates. Reaction was initiated by the addition of enzyme (approx 400 pM final by weight) and substrate (5 μM final) to inhibitor in a total volume of 10 microlitres.

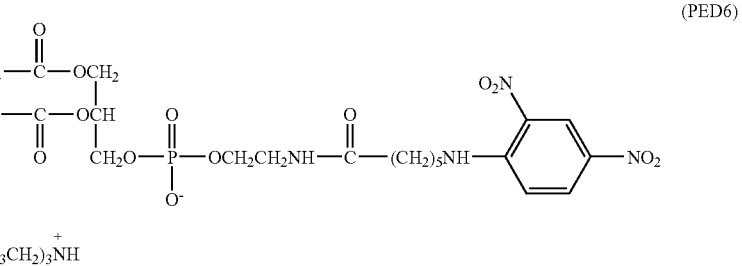

(PED6)

Results

The compounds described in Examples 1-7 were tested as hereinbefore described and were found to have IC₅₀ values in the range 0.1 to 10 nM.

What is claimed is:

1. A compound which is:
   methyl 2-[4-({[2-[2-(2,3-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate;
   ethyl 2-[4-({[2-[2-(2,3-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate;
   ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate;
   ethyl 2-{4-[{[2-[2-(2,4-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate; or
   ethyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate;
   2-[4-({[2-[2-(2,3-Difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoic acid trifluoroacetate, or the free base thereof, or the 2,3-dihydroxybutanedioate salt thereof, or another pharmaceutically acceptable salt of the free base.

2. A pharmaceutical composition comprising a compound of claim 1 or a pharmaceutically acceptable salt thereof and a pharmaceutically acceptable excipient.

3. A compound which is methyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate, or a pharmaceutically acceptable salt thereof.

4. A compound according to claim 3 which is methyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl]-2-methylpropanoate.

5. A compound according to claim 3 which is methyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1[-piperidinyl]-2-methylpropanoate 2,3-dihydroxybutanedioate.

6. A pharmaceutical composition comprising methyl 2-[4-({[2-[2-(2,4-difluorophenyl)ethyl]-4-oxo-1(4H)-quinazolinyl]acetyl} {[4'-(trifluoromethyl)-4-biphenylyl]methyl}amino)-1-piperidinyl[-2-methylpropanoate, or a pharmaceutically acceptable salt thereof.

* * * * *